US006118050A

United States Patent [19]
Sturner et al.

[11] Patent Number: 6,118,050
[45] Date of Patent: Sep. 12, 2000

[54] HYDROXYPHENYLPYRUVATE DIOXYGENASE GENE FROM ARABIDOPSIS AND METHOD OF SCREENING FOR INHIBITORS THEREOF

[75] Inventors: Stephen Sturner, Newtown, Pa.; Lynne Miyo Hirayama, Mercerville, N.J.; Bijay Singh, Hamilton Square, N.J.; Newell Bascomb, Lawrenceville, N.J.

[73] Assignee: American Cyanamid Company, Madison, N.J.

[21] Appl. No.: 08/979,917

[22] Filed: Jul. 25, 1997

Related U.S. Application Data

[60] Provisional application No. 60/022,604, Jul. 25, 1996.
[51] Int. Cl.$^7$ .............................. A01H 5/00; C12N 1/15; C12N 1/21; C12N 5/14; C12N 5/16; C12N 15/29; C12N 15/52; C12N 15/82; C12Q 1/26
[52] U.S. Cl. .................... 800/298; 435/25; 435/252.3; 435/254.11; 435/320.1; 435/325; 435/348; 435/419; 435/420; 536/23.2; 536/23.6
[58] Field of Search ............................ 536/23.2, 23.6; 435/172.3, 320.1, 419, 252.3, 254.11, 348, 325, 25, 420; 800/205, 250, 298

[56] References Cited

U.S. PATENT DOCUMENTS

| | | | |
|---|---|---|---|
| 4,490,838 | 12/1984 | Nishioka et al. | 381/15 |
| 4,535,060 | 8/1985 | Comai | 435/252.33 |
| 4,769,061 | 9/1988 | Comai | 504/206 |
| 5,013,659 | 5/1991 | Bedbrook et al. | 536/23.2 |
| 5,084,082 | 1/1992 | Sebastian | 504/212 |
| 5,786,513 | 7/1998 | Schulz et al. | 568/31 |

FOREIGN PATENT DOCUMENTS

| | | | |
|---|---|---|---|
| 43 05 696 | 9/1994 | Germany . | |
| WO 96/38567 | 12/1996 | WIPO . | |
| WO 97/49816 | 12/1997 | WIPO | C12N 15/53 |

OTHER PUBLICATIONS

Schulz et al., *FEBS Letts.*, 318:162, 1993.
Garcia et al., Biochem. Journal, 325:761–769, 1997.
Barta et al., Pestic. Sci., 48:109–116, 1996.
Lee et al., Weed Science, 45:601–609, 1997.
Bartley et al., Plant Physiol., vol. 114: abstract No. 1587, 1997.
Denoya CD, et al. A *Streptomyces avermitilis* gene encoding a 4–hydroxyphenylpruvic acid dioxygenase–like protein that directs the production of homgentisic acid and an ochronotic pigment in *Escherichia coli*. J. Bacteriol. 176: 5312–5319, Sep. 1994.
Goodwin PH, et al. Brown pigmentation of *Xanthomonis campestris* pv. phaseoli associated with homogentisic acid. Can. J. Microbiol. 40: 28–34, 1995.
De Block M. "The cell biology of plant transformation: Current state, problems, prospects and the implications for plant breeding." Euphytica 71: 1–14, 1993.
Fiedler et al., *Dev. Plant Biol.,* 8:537, 1982.
Fiedler et al., *Planta,* 155:511, 1982.
Ellis et al., *Tox. and Appl. Pharm.,* 133:12, 1995.
Prisbylia et al., Brighton Crop Protection Conference: Weeds, British Crop Protection, Surrey, UK, pp. 731–738, 1993.
Barta et al., *Pest. Sci.* 45:286, 1995.
Soeda et al., *Pestic. Biochem. Physiol.,* 29:35, 1987.
Mayonado et al., *Pestic. Biochem. Physiol.,* 35:138, 1989.
Secor, *Plant Physiol.,* 106:1429, 1994.
Norris et al., *Plant Cell,* 7:2139, 1995.
Elledge et al., *Proc. Natl. Acad. Sci. USA,* 88:1731, 1991.
Amaravadi et al., *BioTechniques,* 16:98, 1994.
Ruetschi et al., *Eur. J. Biochem.,* 205:459, 1992.
Denoya et al., *J. Bacteriol.,* 176:5312, 1994.
Dellaporta et al., *Plant Mol. Biol. Rep.,* 1:19, 1983.
D.N. Glover (ed) *DNA Cloning: A Practical Approach*, vols. I and II, 1985.
M.J. Gait (ed) *Oligunucleotide Synthesis*, 1984.
Hames and Higgins (eds) *Transcription and Translation*, 1984.
Sambrook et al., *Molecular Clong: A Laboratory Manual*, Second Edition, Cold Spring Harbor Laboratory Press, Spring Harbor, New York, 1989.
Perbal, B., A Practical Guide to Molecular Cloning, Second Edition, Wiley Interscience, John Wiley & Sons, New York, NY, 1988.
M. Wolman (ed), *Pigments in Pathology*, Academic Press, NY, 1969.
Blondelle et al., *TibTech,* 14:60, 1996.
Kung, S–D, et al. Transgenic Plants, vol. 1, Engineering and Utilization, Academic Press, Inc., Harcourt Brace Janovich, San Diego, CA, 1993.
L. Mannonen et al., *Critical Reviews in Biotechnology,* 14:287–310, 1994.
An et al., *Plant Mol. Biol. Manual,* A3:1–19 (1988).
Trias et al., *Can. J. Microbiol.,* 35:1037, 1989.

*Primary Examiner*—Amy J. Nelson
*Attorney, Agent, or Firm*—Darby & Darby

[57] ABSTRACT

The present invention provides purified isolated nucleic acids encoding arabidopsis 4-hydroxyphenylpyruvate dioxygenase (HPPD), plasmids encoding HPPD, and transformed cells capable of expressing HPPD. The invention also provides methods for identifying HPPD inhibitors.

10 Claims, 6 Drawing Sheets

FIG. 1A

| | |
|---|---|
| AtHPPD | MGHQNAAVSENQNHDDGAASSPGFKLVGFSKFVRKNPKSDKFKV |
| MOUSE | ..........................MTTYNNKGPKPERGRF.. |
| HUMAN | ..........................MTTYSDKGAKPERGRF.. |
| PIG | ..........................MTSYSDKGEKPERGRF.. |
| S.Aver | ......................MTQTTHHTPDTARQADPFPV |

| | |
|---|---|
| AtHPPD | APYSPSLSAGEIKPTTASIPSFDHGSCRSFFSSHGLGVRAVAI |
| MOUSE | SALN..PWNKEMG................DHLVKHGDGVKDIAF |
| HUMAN | SALN..PWNKEMG................DHLVKHGDGVKDIAF |
| PIG | SALN..PWNKEMG................DHLVKHGDGVKDIAF |
| S.Aver | SVIKPATPWGHFLA................DHVAEHGDGVVDLAI |

| | |
|---|---|
| AtHPPD | SYKAEDTEKSEFLPGFERVEDASSFPLDYGIRRLDHAVGNVP... |
| MOUSE | EKINYTGRFLPGFEAPTYKDTLLPKLPRCNLEIIDHIVGNQPDQ |
| HUMAN | EKMNYIGQFLPGYEAPAFMDPLLPKLPKCSLEMIDHIVGNQPDQ |
| PIG | EKMTFCLDSRPQPSQTLLHRLLLSKLPKCGLEIIDHIVGNQPDQ |
| S.Aver | DRTGYDGPYLPGYVAAA...PIVEPPAHRTFQAIDHCVGNVELG |

| | |
|---|---|
| AtHPPD | KRKSQIQTYLEHNEGAGLQHLALMSEDIFRTLREMRKRSSIGGF |
| MOUSE | RKKSQIQEYVDYNGGAGVQHIALKTEDIITAIRHLRERGTE.... |
| HUMAN | KKKSQIQEYVDYNGGAGVQHIALKTEDIITAIRHLRERGLE.... |
| PIG | KKKSQIQEYVDYNGGAGVQHIALKTEDIITAIRSLRERGVE.... |
| S.Aver | KKKSQIDEYLEFYGGAGVQHIALNTGDIVETVRTMRAAGVQ.... |

| | |
|---|---|
| AtHPPD | DRPTIFIEIIQRVGCMMKDEEGKAYQSGGCGGFGKGNFSELFKS |
| MOUSE | DRPTLFLEVIQRHNHQ.....................GFGAGNFNSLFKA |
| HUMAN | DRPTLFLEVIQRHNHQ.....................GFGAGNFNSLFKA |
| PIG | DRPTVFLEVIQRNNHQ.....................GFGAGNFNSLFKA |
| S.Aver | DRPTVFFEIIERHGSM.....................GFGKGNFKALFEA |

```
KRFHHIEFWCGDATNVARRFSWGLGMRFSAKSDLSTGNMVHASYLLTSGDLRFLFT
LHFHSVTFWVGNAKQAASFYCNKMGFEPLAYRGLETGSREVVSHVIKRGKIVFVLC
LHFHSVTFWVGNAKQAASFYCSKMGFEPLAYRGLETGSREVVSHVIKQGKIVFVLS
LHFHSVTFWVGNAKQAASYCSKIGFEPLAYKGLETGSREVVSHVVKQDKIVFVFS
KGMDAVVFAVGNAKQAA..HYSTAFGMQLVAYSGPENGSRETASYVLTNGSARFVLT

EVEDAESAFSISVANGAIPSSPPIVLN..........EAVTIAEVKLYGDVVLRYV
EVEDCDHIVQKARERGAKIVRE........PWVEQDKFGKVKFAVLQTYGDTTHTLV
EVEDCDYIVQKARERGAKIMRE........PWVEQDKFGKVKFAVLQTYGDTTHTLV
EVEDCDYIVQKARERGAIIVREEVCCAADVRGHHTPLDRAR....QVWEG...TLV
EVPDARAAHAYAIEHGARSVAE........PYELKDEHGTVVLAAIATYGKTRHTLV

ELGPALTYVAGFTGFHQFAEFTADDVGTAESGLNSAVLASNDEMVLLPINEPVHGT
EMQSASEWYLKNLQFHRFWSVDDTQVHTEYSSLRSIVVTNYEESIKMPINEPAPG.
EMVSASEWYLKNLQFHRFWSVDDTQVHTEYSSLRSIVVANYEESIKMPINEPAPG.
EMESASQWYMRNLQFHRFWSVDDTQIHTEYSALRSVVMANYEESIKMPINEPAPG.
RMNEWVGFYNKVMGFTNMKEFVGDDIATEYSALMSKVVADGTLKVKFPINEPALA.

DFMPSPPPTYYQNLKKRVGD..VLSDDQIKECEELGILVDRDDQGTLLQIFTKPLG
..FLAAPSSYYKLLRENLKSAKIQVKESMDVLEELHILVDYDEKGYLLQIFTKPMQ
..FLSVPSTYYKQLREKLKTAKIKVKENIDALEELKILVDYDEKGYLLQIFTKPVQ
..FLAVPFTYYKQLQEKLKSAKIRVKESIDVLEELKILVDYDEKGYLLQIFTKPMQ
..FLDTPDSYYDTLGEWVGDTRVPV....DTLRELKILADRDEDGYLLQIFTKPVQ

IEEYEKTLEAKQLVG*..........
FEEEQALRGNLTDLEPNGVRSGM*
FEEEQNLRGNLTNMETNGVVPGM*
FEEEQELRGNLTDTDPNGVPFRL*
IEREQEKRGNL*..........
```

FIG. 1B

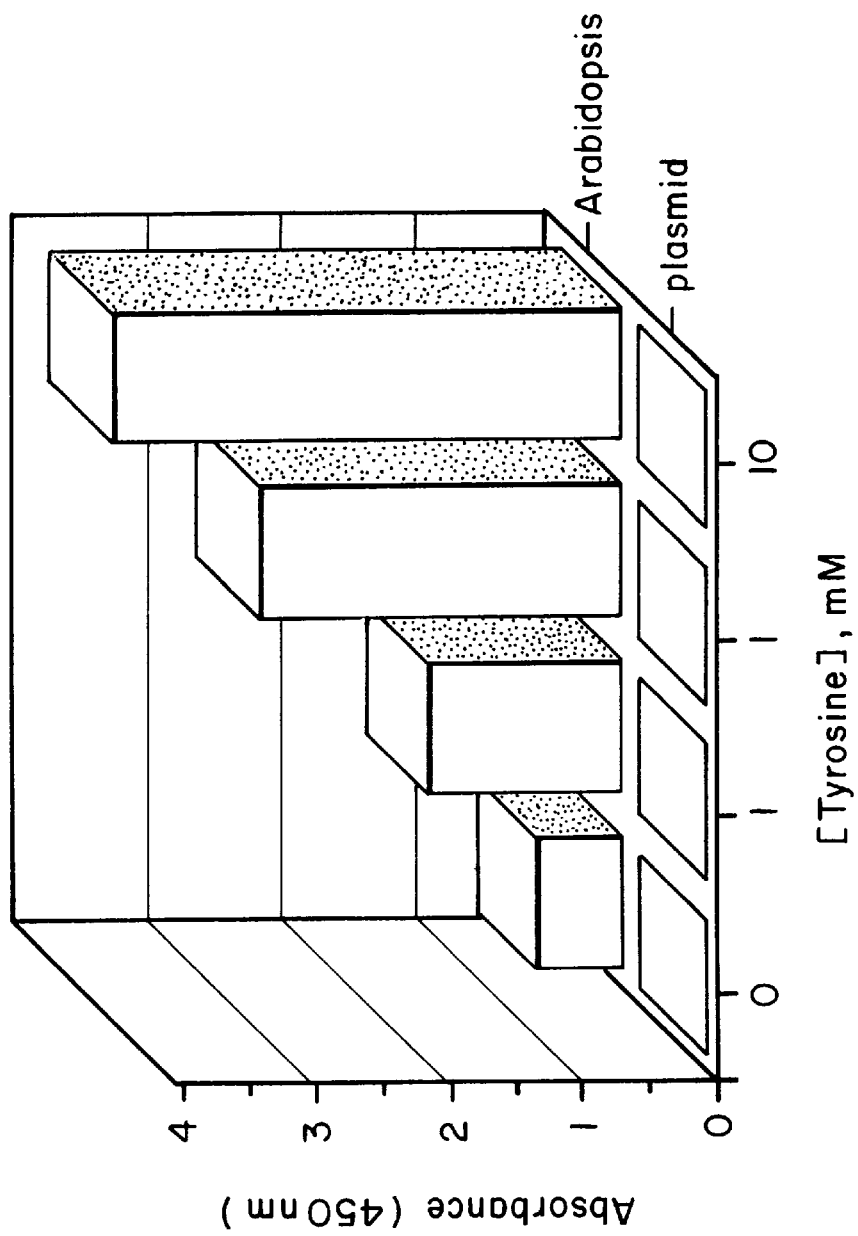

HYDROXYPHENYLPYRUVATE DIOXYGENASE GENE FROM ARABIDOPSIS AND METHOD OF SCREENING FOR INHIBITORS THEREOF

This application claims priority pursuant to 35 U.S.C. §119 from U.S. Provisional application Serial No. 60/022,604 filed Jul. 25, 1996, the entire disclosure of which is hereby incorporated by reference.

FIELD OF THE INVENTION

This invention pertains to DNA encoding 4-hydroxyphenylpyruvate dioxygenase (HPPD), HPPD-inhibiting herbicides, and methods for screening compounds to identify HPPD-inhibiting herbicides. The invention also pertains to HPPD variants that are resistant to the inhibitory action of herbicides, methods for screening for HPPD variants, and plants comprising herbicide-resistant HPPD.

BACKGROUND OF THE INVENTION

In plants, 4-hydroxypenylpyruvate dioxygenase (HPPD, EC 1.13.11.27) is a key enzyme in the biosynthesis of plastoquinones and tocopherols. 4-hydroxyphenylpyruvate acid (derived from chorismic acid via the shikimate pathway) is oxidized and decarboxylated by HPPD to yield homogentisic acid (Fiedler and Schultz, *Dev. Plant Biol.* 8:537, 1982; Fiedler et al., *Planta* 155:511, 1982). Subsequent polyprenylation and decarboxylation of homogentisic acid results in an array of plastoquinones and tocopherols.

In animals, HPPD is involved in tyrosine catabolism. A genetic deficiency in this pathway in humans and mice leads to hereditary tyrosinemia type 1. This disease can be treated by NTBC (2-(2-nitro-4-trifluoromethylbenzoyl)-1,3-cyclohexanedione, an inhibitor of HPPD, which prevents the buildup of intermediates of tyrosine catabolism that are hepatotoxic (Ellis et al., *Tox. and Appl. Pharm.* 133:12, 1995).

Since plastoquinones and tocopherols are essential compounds for plants, inhibitors of this enzyme are potential herbicides. One class of HPPD inhibitors, the triketones, have recently been shown to possess herbicidal activity (Prisbylia et al., *Brighton Crop Protection Conference: Weeds*, British Crop Protection Council, Surrey, UK, pp 731–738, 1993; Schulz et al., *FEBS Letts.* 318:162, 1993). The corn-selective herbicide sulcotrione (2-(2-chloro-4-methanesulfonylbenzoyl)-1,3-cyclohexanedione) causes strong bleaching in susceptible plants accompanied by a loss of carotenoids and chlorophyll with an increase in phytoene and tyrosine (Barta et al., *Pest.Sci.* 45:286, 1995; Soeda et al., *Pestic.Biochem.Physiol.* 29:35, 1987; Mayonado et al., *Pestic.Biochem.Physiol.* 35:138, 1989). Treatment of Lemna with sulcotrione severely inhibited growth and the herbicidal effect could be abolished with homogentisic acid. The partially purified enzyme extracted from maize was shown to be severely inhibited by sulcotrione with a calculated $IC_{50}$ of 45 nM (Schulz et al., 1993, supra). Analysis of partially purified HPPD from barnyardgrass (*Echinochloa crus-galli* L.) showed sulcotrione to be a potent competitive inhibitor of the enzyme with a $K_i$ of 9.8 nM (Secor, *Plant Physiol.* 106:1429, 1994). Canadian Patent Application No. 2,116,421 describes the identification of HPPD inhibitors derived from 2-benzoylcyclohexamine 1,3-diones.

An albino mutant (psdl) isolated from a T-DNA tagged Arabidopsis population was originally selected by virtue of a severe pigment deficiency, which was thought to be due to a defect in carotenoid biosynthetic genes (Norris et al., *Plant Cell* 7:2139, 1995). When the albino psdl mutant was germinated on MS2 medium and subsequently transferred to MS2 medium supplemented with either 4-hydroxyphenylpyruvate (OHPP) or homogentisic acid (HGA), the plants greened on HGA but not OHPP. Further analysis of this mutant indicated that the defect causing the albino phenotype is not due to a mutation in a carotenoid biosynthesis enzyme directly, but rather results from a mutation in HPPD that prevents the biosynthesis of a plastoquinone essential for carotenoid biosynthesis.

Despite the importance of this pathway in plants, genes encoding the plant enzymes for plastoquinone and tocopherol biosynthesis have not previously been isolated. Thus, there is a need in the art for methods and compositions that provide HPPD genes, HPPD inhibitors useful as herbicides, and herbicide-resistant HPPD variants. The present inventors have isolated the gene encoding plant HPPD, have expressed it in *E. coli*, and have demonstrated that bacterially expressed plant HPPD is enzymatically active and that its enzymatic activity is inhibited by triketone herbicides.

BRIEF DESCRIPTION OF THE DRAWINGS

FIGS. 1A and 1B provide an illustration of the amino acid sequence of 4-hydroxyphenylpyruvate dioxygenase (HPPD) from *Arabidopsis thaliana* (AtHPPD) SEQ ID No: 1 and shows the alignment of this sequence with related sequences from mouse, SEQ ID No: 2 human, SEQ ID No: 3 pig, SEQ ID No: 4 and *Streptomyces avermitilis* (S. Aver) SEQ ID No: 5.

FIG. 2 is a graphic illustration of the production of brown pigment by *E. coli* transformed with the Arabidopsis HPPD gene ("Arabidopsis") compared with *E. coli* transformed with a control vector ("plasmid"). The effect on pigment formation of adding increasing concentrations of tyrosine to the culture medium is shown.

FIG. 3A is an illustration of an HPLC elution profile of medium from *E. coli* transformed with a control vector. FIG. 3B is an illustration of an HPLC elution profile of medium from *E. coli* transformed with the Arabidopsis HPPD gene. The elution position of authentic homogentisic acid standard is indicated by an arrow. The insert in FIG. 3B is an illustration of the absorption spectrum of the homogentisic acid peak.

SUMMARY OF THE INVENTION

Figure 3A:
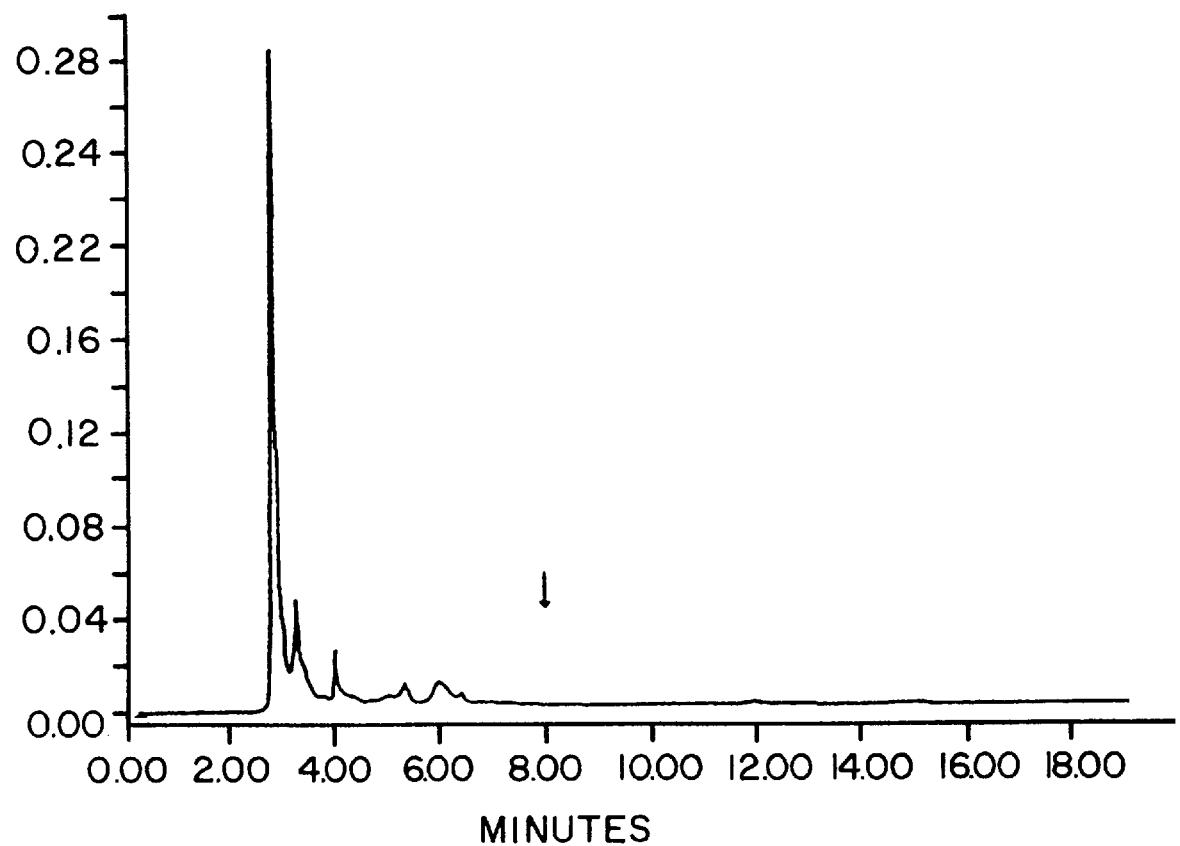
FIGS. 3A–3B are illustrations of HPLC elution profiles.

The present invention provides purified isolated nucleic acids encoding plant 4-hydroxyphenylpyruvate dioxygenase (HPPD), in particular HPPD derived from *Arabidopsis thaliana*, as well as sequence-conservative variants and function-conservative variants thereof; DNA vectors comprising HPPD-encoding nucleic acid operably linked to a transcription regulatory element; and cells comprising the HPPD vectors, including without limitation bacterial, fungal, plant, insect, and mammalian cells. In one embodiment, a bacterial cell expressing high levels of plant HPPD is provided. Also encompassed are HPPD polypeptides and enzymatically active fragments derived therefrom.

In another aspect, the invention provides methods for identifying herbicides/HPPD inhibitors, which are carried out by:

(a) providing a microbial cell expressing plant HPPD;

(b) incubating the cell in the presence of a test compound to form a test culture, and in the absence of a test compound to form a control culture;

(c) monitoring the level of homogentisic acid, or oxidation products thereof, in the test and control cultures; and (d) identifying as a compound that inhibits HPPD any compound that reduces the level of homogentisic acid, or oxidation products thereof, in the test culture relative to the control culture. In the above methods, the monitoring step may be achieved, for example, by measuring the absorbance of said cultures at 450 nm or by visually detecting formation of a brown pigment. Alternatively, an inhibitor is identified as a compound that inhibits the growth of the test culture, wherein the inhibition can be reversed by the addition of homogentistic acid to the culture.

In a further aspect, the invention provides methods for identifying herbicide-resistant HPPD variants, which are carried out by (a) providing a population of cells expressing plant HPPD;

(b) mutagenizing the population of cells;

(c) contacting the mutagenized population of cells with an herbicide, under conditions inhibitory for the growth of non-mutagenized cells;

(d) recovering cells resistant to the inhibitory effects of the herbicide on growth and/or pigment formation; and (e) sequencing HPPD-encoding nucleic acid from the recovered cells. Alternatively, DNA encoding HPPD is subjected to random or site-directed mutagenesis in vitro, followed by expression in a heterologous cell and screening or selection of cells that exhibit herbicide resistance.

In yet another aspect, the invention encompasses variant HPPD proteins that are herbicide-resistant. Preferably, an herbicide-resistant HPPD variant protein, when expressed, in a cell that requires HPPD activity for viability, exhibits (i) catalytic activity alone sufficient to maintain the viability of a cell in which it is expressed; or catalytic activity in combination with any herbicide resistant HPPD variant protein also expressed in the cell, which may be the same as or different than the first HPPD variant protein, sufficient to maintain the viability of a cell in which it is expressed; and (ii) catalytic activity that is more resistant to the herbicide than is wild type HPPD.

Also provided are nucleic acids encoding herbicide-resistant HPPD variants, DNA vectors comprising the nucleic acids, and cells comprising the variant HPPD-encoding vectors. Genes encoding herbicide-resistant HPPD variants can be used as genetic markers, such as, for example, in plasmids and methods for the introduction and selection of any other desired gene.

In another aspect, the present invention provides a method for conferring herbicide resistance on a cell or cells, and particularly a plant cell or cells such as, for example, a seed. An HPPD gene, preferably the *Arabidopsis thaliana* HPPD gene, is mutated to alter the ability of an herbicide to inhibit the enzymatic activity of the HPPD. The mutant gene is cloned into a compatible expression vector, and the gene is transformed into an herbicide-sensitive cell under conditions in which it is expressed at sufficient levels to confer herbicide resistance on the cell.

Also contemplated are methods for weed control, wherein a crop containing an herbicide resistant HPPD gene according to the present invention is cultivated and treated with a weed-controlling effective amount of the herbicide.

DETAILED DESCRIPTION OF THE INVENTION

The present invention encompasses isolated, purified, nucleic acids that encode plant 4-hydroxyphenylpyruvate dioxygenase (HPPD), expression systems in which enzymatically active HPPD is produced, and screening methods for identifying HPPD inhibitors.

The present invention also encompasses methods for screening for and producing plant HPPD variants that are resistant to the inhibitory action of herbicides, DNAs that encode these variants, vectors that include these DNAs, the HPPD variant proteins, and cels that express these variants. Additionally provided are methods for producing herbicide resistance in plants by expressing these variants and methods of weed control.

Isolation and Characterization of the Gene Encoding Arabidopsis HPPD

The present inventors have isolated and sequenced the gene encoding *Arabidopsis thaliana* HPPD, using the methods outlined below. Briefly, an *Arabidopsis thaliana* λ Yes cDNA library (Elledge et al., *Proc. Natl. Acad. Sci. USA* 88:1731, 1991) was screened using a PCR-based method (Amaravadi et al., *Bio Techniques* 16:98, 1994).

Primers: A forward primer, designated ATHPPD1F (5'-CGTGCTCAGCGATGATCAGA-3' SEQ ID No: 6) and a reverse primer, designated ATHPPD1R (5'-CGGCCTGTCACCTAGTGGTT-3' SEQ ID No: 7) were synthesized based on an Arabidopsis EST sequence (GenBank ID No: T20952) that showed homology to mammalian HPPD sequences.

The primers were evaluated in a polymerase chain reaction (PCR) using as template DNA a 1 μl aliquot (containing 3×10$^6$ pfu/ml) of the cDNA phage library. For PCR, a 50 μl reaction contained 1×PCR Buffer, 200 mM of each deoxynucleoside triphosphate, 1.25 units of AmpliTaq DNA Polymerase (all from Perkin Elmer), and 7.5 pmoles of each primer. The reaction mixture was heated to 95° C. for 2 min and amplified using 35 cycles of: 95° C. for 1 min, 48° C. for 2 min, 72° C. for 1 min 30 sec. This was followed by incubation at 72° C. for 7 min. A fragment of the predicted size of 112 bp was produced. This fragment was cloned into the pCRII vector (TA Cloning Kit, Invitrogen) and sequenced, and was found to be identical to the Arabidopsis EST sequence (with the addition of 3 residues which had been undetermined in the reported sequence of the EST).

Library screening: The cDNA library was plated on 13 plates containing NZCYM agar at a density of 40,000 pfu/plate. The phage from each plate were eluted into SM, and aliquots from the 13 individual pools of phage were used as templates for PCR with the ATHPPD1F and ATHPPD1R primer pair. PCR conditions were as described above. (In the first round, 1 μl of each of the eluted phage pools was used as template, and 5 μl were used in subsequent rounds). In the first round, ten of the thirteen phage pools were positive by PCR. One of the positive pools was selected for further screening. In the second round, the eluates from 10 plates of 5,000 pfu/plate gave 1 positive pool. In the third round, 10 plates of about 20 pfu/plate gave 2 positive pools. The third round positive pools were plated out, and 36 individual plaques were picked and screened to find a single HPPD positive plaque. The insert-bearing plasmid was excised from this phage via the automatic subcloning properties of the vector. Restriction analysis indicated that this plasmid contained a 1.5 kb insert.

Sequence Analysis: Template DNA for sequencing was prepared using the Wizard DNA Purification System (Promega). Sequencing reactions were carried out using the fmol DNA Sequencing System (Promega), and sequence gels were run on Hydrolink Long Ranger (AT Biochem) gels. The insert of the HPPD-containing plasmid isolated from the cDNA library was sequenced using two primers that hybridize to the λ Yes vector on opposite sides of the XhoI cloning site in addition to a series of internal primers: ATHPPD1F ATHPPD1R as above; and ATHPPD2F (5'-CTTCTACCGATTAACGAGCCAGTG-3' SEQ ID No: 8);
ATHPPD2R (5'-CACTGGCTCGTTAATCGGTAGAAG-3' SEQ ID No: 9);
ATHPPD3F (5'-TCCATCACATCGAGTTCTGGTGCG-3' SEQ ID No: 10);
ATHPPD3R (5'-AAAAGGAATCGGAGGTCACCGGA-3' SEQ ID No: 11);
ATHPPD4F (5'-CTGAGGTTAAACTATACGGCGA-3' SEQ ID No: 12); and
ATHPPD4R (5'-TCGCCGTATAGTTTAACCTCAG-3' SEQ ID No: 13). All sequence information was confirmed by sequencing both strands. Translation of the HPPD nucleotide sequence, sequence comparisons, and multiple sequence alignments were performed using the software in The Wisconsin Package, Version 8.0 (Genetics Computer Group, Madison, Wis.).

The results indicated that the 1.5 kb insert contains an open reading frame of 445 amino acids (FIG. 1). A TFASTA search of the GenEMBL Database identified five known sequences as having partial homology: Streptomyces HPPD (U11864); rat F alloantigen (M18405), mouse HPPD (D29987); pig HPPD (D13390); and human HPPD (X72389). Direct pairwise comparisons of the Arabidopsis sequence with those mentioned above showed a 56% average similarity and a 37% average identity. Additionally, a number of conserved tyrosine and histidine residues, which have been proposed as metal-binding sites in mammalian HPPD (Ruetschi et at., *Eur.J.Biochem.* 205:459, 1992; Denoya et al., *J. Bacteriol.* 176:5312, 1994), are also observed in the Arabidopsis sequence.

Genomic organization of HPPD gene in Arabidopsis: Southern blot analysis was performed using genomic DNA prepared from Arabidopsis seedings according to the method of Dellaporta (Dellaporta et al., *Plant Mol. Biol.* Rep. 1: 19, 1983). 10 μg of DNA were digested with the restriction enzymes BamHI, EcoRI and HindIII, after which the digests were separated on a 0.9% agarose gel, transferred to a Duralon-UV Membrane (Stratagene) using the VacuGene XI Vacuum blotting System (Pharmacia) and crosslinked using the Stratalinker UV Crosslinker (Stratagene). The HPPD probe was prepared by: (i) gel purifying (using GeneClean Kit, Bio 101, Inc.) the XhoI/SstI fragment from the digest of HPPD/λ Yes plasmid DNA. The fragment contains 50 bases of sequence upstream of the ATG start codon and extends to a position 55 bases upstream of the TGA stop codon; and (ii) labeling the fragment using the Prime-It Fluor Fluorescence Labeling kit (Stratagene). The labelled probe was hybridized to the membrane for 2 hours at 68° C. using the QuikHyb Rapid Hybridization Solution (Stratagene). The membrane was washed with 0.1× SSC/0.1% SDS once at room temperature and twice at 60° C., after which hybridization was visualized using the Illuminator Nonradioactive Detection System (Stratagene).

Only a single band hybridized to the probe under high stringency conditions in both the BamHI and HindiIII digests. Two bands were observed in the EcoRI digest, reflecting the presence of an internal EcoRI site in the HPPD sequence. These results suggested that HPPD is encoded by a single-copy gene in Arabidopsis.

The entire HPPD coding sequence was then amplified from Arabidopsis genomic DNA using primers ATHPPD5F (5'-CCATGGGCCACCAAAACG-3' SEQ ID No: 14) and ATHPPD5R (5'-CTGCAGTCATCCCACTAACTGTTTG-3' SEQ ID No: 15). The resulting genomic HPPD fragment, which was slightly larger than the corresponding cDNA fragment, was cloned into the pCRII vector (TA Cloning Kit, Invitrogen) and sequenced. A single intron of 107 bp was detected, located at nucleotide position 1163–1164 of the cDNA sequence.

Nucleic Acids, Vectors, Expression Systems, and Polypeptides

In practicing the present invention, many techniques in molecular biology, microbiology, recombinant DNA, and protein biochemistry such as these explained fully in, for example, Sambrook et al., 1989, *Molecular Cloning: A Laboratory Manual*, Second Edition, Cold Spring Harbor Laboratory Press, Cold Spring Harbor, N.Y.; *DNA Cloning: A Practical Approach,* Volumes I and II, 1985 (D. N. Glover ed.); *Oligonucleotide Synthesis,* 1984, (M. L. Gait ed.); *Transcription and Translation,* 1984 (Hames and Higgins eds.); *A Practical Guide to Molecular Cloning;* the series, *Methods in Enzymology* (Academic Press, Inc.); and *Protein Purfication: Principles and Practice*, Second Edition (Springer-Verlag, N.Y.), are used.

The present invention encompasses nucleic acid sequences encoding plant HPPD, enzymatically active fragments derived therefrom, and related HPPD-derived sequences from other plant species. As used herein, a nucleic acid that is "derived from" an HPPD sequence refers to a nucleic acid sequence that corresponds to a region of the sequence, sequences that are homologous or complementary to the sequence, and "sequence -conservative variants" and "function-conservative variants". Sequence-conservative variants are those in which a change of one or more nucleotides in a given codon position results in no alteration in the amino acid encoded at that position. Function-conservative variants are those in which a given amino acid residue in HPPD has been changed without altering the overall conformation and function of the HPPD polypeptide, including, but not limited to, replacement of an amino acid with one having similar physico-chemical properties (such as, for example, acidic, basic, hydrophobic, and the like). Fragments of HPPD that retain enzymatic activity can be identified according to the methods described herein, e.g., expression in *E. coli* followed by enzymatic assay of the cell extract.

HPPD sequences derived from plants other than *Arabidopsis thaliana* can be isolated by routine experimentation using the methods and compositions provided herein. For example, hybridization of a nucleic acid comprising all or part of the Arabidopsis HPPD sequence under conditions of intermediate stringency (such as, for example, an aqueous solution of 2× SSC at 65° C.) to cDNA or genomic DNA derived from other plant species can be used to identify HPPD homologues. cDNA libraries derived from different plant species are commercially available (Clontech, Palo Alto, Calif.; Stratagene, La Jolla, Calif.). Alternatively, PCR-based methods can be used to amplify HPPD-related sequences from cDNA or genomic DNA derived from other plants. Expression of the identified sequence in, e.g., *E. coli,* using methods described in more detail below, is then performed to confirm that the enzymatic activity of the polypeptide encoded by the sequence corresponds to that of HPPD. Accordingly, HPPD sequences derived from dicotyledonous and monocotyledenous plants are within the scope of the invention.

The nucleic acids of the present invention include purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases. The nucleic acids may be isolated directly from cells. Alternatively, PCR can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural Arabidopsis regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed HPPD sequences or derivatives or fragments thereof. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Suitable host cells may be transformed/transfected/ infected as appropriate by any suitable method including electroporation, $CaCl_2$ mediated DNA uptake, fungal infection, microinjection, microprojectile, or other established methods.

Appropriate host cells include bacteria, archebacteria, fungi, especially yeast, and plant and animal cells, especially mammalian cells. Of particular interest are *E. coli, B. Subtilis, Saccharomyces cerevisiae, Saccharomyces carlsbergensis, Schizosaccharomyces pombi*, SF9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced HPPD-derived peptides and polypeptides.

Advantageously, vectors may also include a transcription regulatory element (i.e., a promoter) operably linked to the HPPD portion. The promoter may optionally contain operator portions and/or ribosome binding sites. Non-limiting examples of bacterial promoters compatible with *E. coli* include: trc promoter, β-lactamase (penicillinase) promoter; lactose promoter; tryptophan (trp) promoter; arabinose BAD operon promoter; lambda-derived P1 promoter and N gene ribosome binding site; and the hybrid tac promoter derived from sequences of the trp and lac Uv5 promoters. Non-limiting examples of yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences, and enhancer sequences which increase expression may also be included. Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included.

Nucleic acids encoding wild-type or variant HPPD polypeptides may also be introduced into cells by recombination events. For example, such a sequence can be introduced into a cell, and thereby effect homologous recombination at the site of an endogenous gene or a sequence with substantial identity to the gene. Other recombination-based methods, such as non-homologous recombinations or deletion of endogenous genes by homologous recombination, may also be used.

HPPD-derived polypeptides according to the present invention, including function-conservative variants of HPPD, may be isolated from wild-type or mutant Arabidopsis cells, or from heterologous organisms or cells (including, but not limited to, bacteria, fungi, insect, plant, and mammalian cells) into which an HPPD-derived protein-coding sequence has been introduced and expressed. Furthermore, the polypeptides may be part of recombinant fusion proteins. Alternatively, polypeptides may be chemically synthesized by commercially available automated procedures, including, without limitation, exclusive solid phase synthesis, partial solid phase methods, fragment condensation or classical solution synthesis.

"Purification" of an HPPD polypeptide refers to the isolation of the HPPD polypeptide in a form that allows its enzymatic activity to be measured without interference by other components of the cell in which the polypeptide is expressed. Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the HPPD protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against HPPD against peptides derived therefrom can be used as purification reagents. Other purification methods are possible.

The present invention also encompasses derivatives and homologues of HPPD polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

Screening Methods to Identify HPPD Inhibitors/Herbicides

The methods and compositions of the present invention can be used to identify compounds that inhibit the function of HPPD and thus are useful as herbicides or as lead compounds for the development of useful herbicides. This is achieved by providing a cell that expresses HPPD and thereby produces homogentisic acid from 4-hydroxyphenylpyruvate (OHPP). Cell cultures expressing HPPD are incubated in the presence of test compounds to form test cultures, and in the absence of test compounds to form control cultures. Incubation is allowed to proceed for a sufficient time and under appropriate conditions to allow for interference with HPPD function. At a predetermined time after the start of incubation with a test compound, an assay is performed to monitor HPPD enzymatic activity. In a preferred embodiment, HPPD activity is monitored visually, by the appearance of red-brown pigments produced by oxidation and/or polymerization of homogentisic acid (La Du et al., in *Ochronosis. Pigments in Pathology*, M. Wolman (ed), Academic Press, N.Y., 1969). Alternatively, HPPD enzymatic activity may be monitored in cell extracts, using conventional assays such as that described in Example 1 below. Additional controls, with respect to both culture samples and assay samples, are also included, such as, for example, a host cell not expressing HPPD (e.g., a host cell transformed with an expression plasmid containing the HPPD gene in a reverse orientation or with no insert). HPPD inhibitory compounds are identified as those that reduce HPPD activity in the test cultures relative to the control cultures.

Host cells that may be used in practicing the present invention include without limitation bacterial, fungal, insect, mammalian, and plant cells. Preferably, bacterial cells are used. Most preferably, the bacterial cell is a variant (such as, e.g., the imp mutant of *E. coli*) that exhibits increased membrane permeability for test compounds relative to a wild-type host cell.

Preferably, the methods of the present invention are adapted to a high-throughput screen, allowing a multiplicity of compounds to be tested in a single assay. Such inhibitory compounds may be found in, for example, natural product libraries, fermentation libraries (encompassing plants and microorganisms), combinatorial libraries, compound files, and synthetic compound libraries. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (NC), or are readily producible. Additionally, natural and synthetically produced libraries and compounds are readily modified through conventional chemical, physical, and biochemical means (Blondelle et al., *TibTech* 14:60, 1996). HPPD inhibitor assays according to the present invention are advantageous in accommodating many different types of solvents and thus allowing the testing of compounds from many sources.

Once a compound has been identified by the methods of the present invention as an HPPD inhibitor, in vivo and in vitro tests may be performed to further characterize the nature and mechanism of the HPPD inhibitory activity. For example, the effect of an identified compound on in vitro enzymatic activity of purified or partially purified HPPD may be determined as described in Example 1 below. Classical enzyme kinetic plots can be used to distinguish, e.g., competitive and non-competitive inhibitors.

Compounds identified as HPPD inhibitors using the methods of the present invention may be modified to enhance potency, efficacy, uptake, stability, and suitability for use in commercial herbicide applications, etc. These modifications are achieved and tested using methods well-known in the art.

Isolation of Herbicide-Resistant HPPD Variants

The present invention encompasses the isolation of HPPD variants that are resistant to the action of HPPD inhibitors/herbicides. The HPPD variants may be naturally occurring or may be obtained by random or site-directed mutagenesis.

In one embodiment, a population of cells or organisms expressing HPPD is mutagenized using procedures well-known in the art, after which the cells or organisms are subjected to a screening or selection procedure to identify those that are resistant to the toxic effects of an HPPD inhibitor. The variant HPPD gene is then isolated from the resistant cell or organism using, e.g., PCR techniques.

In another embodiment, an isolated HPPD gene is subjected to random or site-directed mutagenesis in vitro, after which mutagenized versions of the gene are re-introduced into an appropriate cell such as, e.g., *E. coli,* and the cells are subjected to a selection or screening procedure as above.

The variant HPPD genes are expressed in an appropriate host cell, and the enzymatic properties of variant HPPD polypeptides are compared to the wild-type HPPD. Preferably, a given mutation results in an HPPD variant polypeptide that retains in vitro enzymatic activity towards 4-hydroxphenylpyruvic acid (OHPP), i.e., the conversion of OHPP to homogentisic acid (and thus is expected to be biologically active in vivo), while exhibiting catalytic activity that is relatively more resistant to the selected herbicide (s) than is wild-type HPPD. Preferably, when expressed in a cell that requires HPPD activity for viability, the variant HPPD exhibits (i) catalytic activity alone sufficient to maintain the viability of a cell in which it is expressed; or catalytic activity in combination with any herbicide resistant HPPD variant protein also expressed in the cell, which may be the same as or different than the first HPPD variant protein, sufficient to maintain the viability of a cell in which it is expressed; and (ii) catalytic activity that is more resistant to the herbicide than is wild type HPPD.

Therefore, any one specific HPPD variant protein need not have the total catalytic activity necessary to maintain the viability of the cell, but must have some catalytic activity in an amount, alone or in combination with the catalytic activity of additional copies of the same HPPD variant and/or the catalytic activity of other HPPD variant protein (s), sufficient to maintain the viability of a cell that requires HPPD activity for viability. For example, catalytic activity may be increased to minimum acceptable levels by introducing multiple copies of a variant encoding gene into the cell or by introducing the gene which further includes a relatively strong promoter to enhance the production of the variant.

More resistant means that the catalytic activity of the variant is diminished by the herbicide(s), if at all, to a lesser degree than wild-type HPPD catalytic activity is diminished by the herbicide(s). Preferred more resistant variant HPPD retains sufficient catalytic to maintain the viability of a cell, plant, or organism wherein at the same concentration of the same herbicide(s), wild-type HPPD would not retain sufficient catalytic activity to maintain the viability of the cell, plant, or organism.

Preferably the catalytic activity in the absence of herbicide(s) is at least about 5% and, most preferably, is more than about 20% of the catalytic activity of the wild-type HPPD in the absence of herbicide(s).

In the case of triketone-resistant variant HPPD, it is preferred that the HPPD variant protein has (i) catalytic activity in the absence of said herbicide of more than about 20% of the catalytic activity of said wild-type HPPD; and (ii) catalytic activity that is relatively more resistant to presence of triketone herbicides compared to wild type HPPD.

Herbicide-resistant HPPD variants can be used as genetic markers in any cell that is normally sensitive to the inhibitory effects of the herbicide on growth and/or pigment formation. In one embodiment, DNA encoding an herbicide-resistant HPPD variant is incorporated into a plasmid under the control of a suitable promoter. Any desired gene can then be incorporated into the plasmid, and the the final recombinant plasmid introduced into an herbicide-sensitive cell. Cells that have been transformed with the plasmid are then selected or screened by incubation in the presence of a concentration of herbicide sufficient to inhibit growth and/or pigment formation.

Chemical-resistant Plants and Plants Containing Variant HPPD Genes

The present invention encompasses transgenic cells, including, but not limited to seeds, organisms, and plants into which genes encoding herbicide-resistant HPPD variants have been introduced. Non-limiting examples of suitable recipient plants are listed in Table 1 below:

TABLE 1

RECIPIENT PLANTS

| COMMON NAME | FAMILY | LATIN NAME |
|---|---|---|
| Maize | Gramineae | Zea mays |
| Maize, Dent | Gramineae | Zea mays dentiformis |
| Maize, Flint | Gramineae | Zea mays vulgaris |
| Maize, Pop | Gramineae | Zea mays microsperma |
| Maize, Soft | Gramineae | Zea mays amylacea |
| Maize, Sweet | Gramineae | Zea mays amyleasaccharata |
| Maize, Sweet | Gramineae | Zea mays saccharate |
| Maize, Waxy | Gramineae | Zea mays ceratina |
| Wheat, Dinkel | Pooideae | Triticum spelta |
| Wheat, Durum | Pooideae | Triticum durum |
| Wheat, English | Pooideae | Triticum turgidum |
| Wheat, Large Spelt | Pooideae | Triticum spelta |
| Wheat, Polish | Pooideae | Triticum polonium |
| Wheat, Poulard | Pooideae | Triticum turgidum |
| Wheat, Singlegrained | Pooideae | Triticum monococcum |
| Wheat, Small Spelt | Pooideae | Triticum monococcum |
| Wheat, Soft | Pooideae | Triticum aestivum |
| Rice | Gramineae | Oryza sativa |
| Rice, American Wild | Gramineae | Zizania aquatica |
| Rice, Australian | Gramineae | Oryza australiensis |
| Rice, Indian | Gramineae | Zizania aquatica |
| Rice, Red | Gramineae | Oryza glaberrima |
| Rice, Tuscarora | Gramineae | Zizania aquatica |
| Rice, West African | Gramineae | Oryza glaberrima |
| Barley | Pooideae | Hordeum vulgare |
| Barley, Abyssinian Intermediate, also Irregular | Pooideae | Hordeum irregulare |
| Barley, Ancestral Tworow | Pooideae | Hordeum spontaneum |
| Barley, Beardless | Pooideae | Hordeum trifurcatum |
| Barley, Egyptian | Pooideae | Hordeum trifurcatum |
| Barley, fourrowed | Pooideae | Hordeum vulgare polystichon |
| Barley, sixrowed | Pooideae | Hordeum vulgare hexastichon |
| Barley, Tworowed | Pooideae | Hordeum distichon |
| Cotton, Abroma | Dicotyledoneae | Abroma augusta |
| Cotton, American Upland | Malvaceae | Gossypium hirsutum |
| Cotton, Asiatic Tree, also Indian Tree | Malvaceae | Gossypium arboreum |
| Cotton, Brazilian, also, Kidney, and, Pernambuco | Malvaceae | Gossypium barbadense brasiliense |
| Cotton, Levant | Malvaceae | Gossypium herbaceum |
| Cotton, Long Silk, also Long Staple, Sea Island | Malvaceae | Gossypium barbadense |
| Cotton, Mexican, also Short Staple | Malvaceae | Gossypium hirsutum |
| Soybean, Soya | Leguminosae | Glycine max |
| Sugar beet | Chenopodiaceae | Beta vulgaris altissima |
| Sugar cane | Woody-plant | Arenga pinnata |
| Tomato | Solanaceae | Lycopersicon esculentum |
| Tomato, Cherry | Solanaceae | Lycopersicon esculentum cemsiforme |
| Tomato, Common | Solanaceae | Lycoprsicon esculentum commune |
| Tomato, Currant | Solanaceae | Lycopersicon pimpinellifolium |
| Tomato, Husk | Solanaceae | Physalis ixocarpa |
| Tomato, Hyenas | Solanaceae | Solanum incanum |
| Tomato, Pear | Solanaceae | Lycopersicon esculentum pyriforme |
| Tomato, Tree | Solanaceae | Cyphomandra betacea |
| Potato | Solanaceae | Solanum tuberosum |
| Potato, Spanish, Sweet potato | Convolvulaceae | Ipomoea batatas |
| Rye, Common | Pooideae | Secale cereale |
| Rye, Mountain | Pooideae | Secale montanum |
| Pepper, Bell | Solanaceae | Capsicum annuum grossum |
| Pepper, Bird, also | Solanaceae | Capsicum annuum |

TABLE 1-continued

RECIPIENT PLANTS

| COMMON NAME | FAMILY | LATIN NAME |
|---|---|---|
| Cayenne, Guinea Pepper, Bonnet | Solanaceae | *minimum Capsicum sinense* |
| Pepper, Bullnose, also Sweet | Solanaceae | *Capsicum annuum grossum* |
| Pepper, Cherry | Solanaceae | *Capsicum annuum cerisiforme* |
| Pepper, Cluster, also Red Cluster | Solanaceae | *Capsicum annuum fasciculatum* |
| Pepper, Cone | Solanaceae | *Capsicum annuum conoides* |
| Pepper, Goat, also Spur | Solanaceae | *Capsicum frutescens* |
| Pepper, Long | Solanaceae | *Capsicum frutescens longum* |
| Pepper, Oranamental Red, also Wrinkled | Solanaceae | *Capsicum annuum abbreviatum* |
| Pepper, Tabasco Red | Solanaceae | *Capsicum annuum conoides* |
| Lettuce, Garden | Compositae | *Lactuca sativa* |
| Lettuce, Asparagus, also Celery | Compositae | *Lactuca sativa asparagina* |
| Lettuce, Blue | Compositae | *Lactuca perennis* |
| Lettuce, Blue, also Chicory | Compositae | *Lactuca pulchella* |
| Lettuce, Cabbage, also Head | Compositae | *Lactuca sativa capitata* |
| Lettuce, Cos, also Longleaf, Romaine | Compositae | *Lactuca sativa longifolia* |
| Lettuce, Crinkle, also Curled, Cutting, Leaf | Compositae | *Lactuca sativa crispa* |
| Celery | Umbelliferae | *Apium graveolens dulce* |
| Celery, Blanching, also Garden | Umbelliferae | *Apium graveolens dulce* |
| Celery, Root, also Turniprooted | Umbelliferae | *Apium graveolens rapaceum* |
| Eggplant, Garden | Solanaceae | *Solanum melongena* |
| Sorghum | Sorghum | All crop species |
| Alfalfa | Leguminosae | *Medicago sativum* |
| Carrot | Umbelliferae | *Daucus carota sativa* |
| Bean, Climbing | Leguminosae | *Phaseolus vulgaris vulgaris* |
| Bean, Sprouts | Leguminosae | *Phaseolus aureus* |
| Bean, Brazilian Broad | Leguminosae | *Canavalia ensiformis* |
| Bean, Broad | Leguminosae | *Vicia faba* |
| Bean, Common, also French, White, Kidney | Leguminosae | *Phaseolus vulgaris* |
| Bean, Egyptian | Leguminosae | *Dolichos lablab* |
| Bean, Long, also Yardlong | Leguminosae | *Vigna sesquipedalis* |
| Bean, Winged | Leguminosae | *Psophocaipus tetragonolobus* |
| Oat, also Common, Side, Tree | Avena | Sativa |
| Oat, Black, also Bristle, Lopsided | Avena | Strigosa |
| Oat, Bristle | Avena | |
| Pea, also Garden, Green, Shelling | Leguminosae | *Pisum, sativum sativum* |
| Pea, Blackeyed | Leguminosae | *Vigna sinensis* |
| Pea, Edible Podded | Leguminosae | *Pisum sativum axiphium* |
| Pea, Grey | Leguminosae | *Pisum sativum speciosum* |
| Pea, Winged | Leguminosae | *Tetragonolobus purpureus* |
| Pea, Wrinkled | Leguminosae | *Pisum sativum medullar* |
| Sunflower | Compositae | *Helianthus annuus* |
| Squash, Autumn, Winter | Dicotyledoneae | *Cucurbita maxima* |
| Squash, Bush, also Summer | Dicotyledoneae | *Cucurbita pepo melopepo* |
| Squash, Turban | Dicotyledoneae | *Cucurbita maxima turbaniformis* |
| Cucumber | Dicotyledoneae | *Cucumis sativus* |
| Cucumber, African, also Bitter | | *Momordica charantia* |
| Cucumber, Squirting, also Wild | | *Ecballium elaterium* |
| Cucumber, Wild | | *Cucumis anguria* |
| Poplar, California | Woody-Plant | *Populus trichocarpa* |
| Poplar, European | | *Populus nigra* |

TABLE 1-continued

RECIPIENT PLANTS

| COMMON NAME | FAMILY | LATIN NAME |
|---|---|---|
| Black Poplar, Gray | | *Populus canescens* |
| Poplar, Lombardy | | *Populus italica* |
| Poplar, Silverleaf, also White | | *Populus alba* |
| Poplar, Western Balsam | | *Populus trichocarpa* |
| Tobacco | Solanaceae | Nicotiana |
| Arabidopsis Thaliana | Cruciferae | *Arabidopsis thaliana* |
| Turfgrass | Lolium | |
| Turfgrass | Agrostis | |
| | Other families of turfgrass | |
| Clover | Leguminosae | |

Expression of the variant HPPD polypeptides in transgenic plants confers a high level of resistance to herbicides including, but not limited to, triketone herbicides such as, for example, sulcotrione, allowing the use of these herbicides during cultivation of the transgenic plants.

Methods for the introduction of foreign genes into plants are known in the art. Non-limiting examples of such methods include Agrobacterium infection, particle bombardment, polyethylene glycol (PEG) treatment of protoplasts, electroporation of protoplasts, microinjection, macroinjection, tiller injection, pollen tube pathway, dry seed imbibition, laser perforation, and electrophoresis. These methods are described in, for example, B. Jenes et al., and S. W. Ritchie et al. In *Transgenic Plants, Vol. 1, Engineering and Utilization,* ed. S.-D. Kung, R. Wu, Academic Press, Inc., Harcourt Brace Jovanovich 1993; and L. Mannonen et al., *Critical Reviews in Biotechnology,* 14:287–310, 1994.

In a preferred embodiment, the DNA encoding a variant HPPD is cloned into a DNA vector containing an antibiotic resistance marker gene, and the recombinant HPPD DNA-containing plasmid is introduced into *Agrobacterium tumefaciens* containing a Ti plasmid. This "binary vector system" is described in, for example, U.S. Pat. No. 4,490,838, and in An et al., *Plant Mol.Biol.Manual* A3:1–19 (1988). The transformed Agrobactetium is then co-cultivated with leaf disks from the recipient plant to allow infection and transformation of plant cells. Transformed plant cells are then cultivated in regeneration medium, which promotes the formation of shoots, first in the presence of the appropriate antibiotic to select for transformed cells, then in the presence of herbicide. In plant cells successfully transformed with DNA encoding herbicide-resistant HPPD, shoot formation occurs even in the presence of levels of herbicide that inhibit shoot formation from non-transformed cels. After confiming the presence of variant HPPD DNA using, for example, polymerase chain reaction (PCR) analysis, transformed plants are tested for their ability to withstand herbicide spraying and for their capabilities for seed germination and root initiation and proliferation in the presence of herbicide.

The methods and compositions of the present invention can be used for the production of herbicide-resistant HPPD variants, which can be incorporated into plants to confer selective herbicide resistance on the plants. Intermediate variants of HPPD (for example, variants that exhibit sub-optimal specific activity but high herbicide resistance, or the converse) are useful as templates for the design of second-generation HPPD variants that retain adequate specific activity and high resistance.

Herbicide resistant HPPD genes can be transformed into crop species in single or multiple copies to confer herbicide resistance. Genetic engineering of crop species with reduced sensitivity to herbicides can:

(1) Increase the spectrum and flexibility of application of specific effective and environmentally benign herbicides;

(2) Enhance the commercial value of these herbicides;

(3) Reduce weed pressure in crop fields by effective use of herbicides on herbicide resistant crop species and a corresponding increase in harvest yields;

(4) Increase sales of seed for herbicide-resistant plants;

(5) Increase resistance to crop damage from carry-over of herbicides applied in a previous planting;

(6) Decrease susceptibility to changes in herbicide characteristics due to adverse climate conditions; and (7) Increase tolerance to unevenly or mis-applied herbicides.

For example, transgenic HPPD variant protein containing plants can be cultivated. The crop can be treated with a weed controlling effective amount of the herbicide to which the HPPD variant transgenic plant is resistant, resulting in weed control in the crop without detrimentally affecting the cultivated crop.

DESCRIPTION OF THE PREFERRED EMBODIMENTS

The following examples are intended to illustrate the present invention without limitation.

EXAMPLE 1

Expression of Arabidopsis HPPD in *E. coli*

The following experiments were performed to demonstrate the production of high levels of enzymatically active Arabidopsis HPPD in *E. coli*.

A. Cloning and Bacterial Transformation:

The HPPD coding sequence was cloned into the pKK233-2 expression vector (Clontech) so that the ATG initiation codon of HPPD was in-frame with the trc promoter using a PCR-based method. A primer designated ATHPPD6F (5'GAAAT$\underline{CC}$ATGGCACCAAAACG-3' SEQ ID No: 16), which hybridizes in the region of the HPPD start codon (in bold), includes a single base change (C from A, in italic) to generate an NcoI site (underlined). The primer ATHPPD6R (5'-CTTCT$\underline{CCATGG}$TCATCCCACTAACTGT-3' SEQ ID No: 17), which hybridizes in the region of the HPPD stop codon (in bold), includes an NcoI site outside the coding region (underlined).

A PCR reaction was performed using the above primers and, as template DNA, the HPPD sequence isolated from the cDNA library screen described above. The reaction mixture (100 μl) contained the following components: 2 ng plasmid DNA; 1×PCR buffer; 200 mM each deoxynucleotide triphosphate; 2.5 units AmpliTaq DNA Polymerase (Perkin Elmer); 13 pmol of primer ATHPPD6F; and 11 pmol of primer ATHPPD6F. The reaction mixture was heated to 95° C. for 2 min, and then was amplified using 30 cycles of: 95° C., 1 min; 55° C., 2 min; 72° C., 1.5 min. This was followed by incubation at 72° C. for 7 min.

A 1.3 kb PCR product was amplified. The fragment was resolved on a 1.2% Nu Sieve GTG gel (FMC) and was purified (GeneClean, Bio 101). The purified fragment was digested with NcoI and was ligated into NcoI-digested, alkaline phosphatase-treated pKK233-2 vector (Clontech).

The ligation mixture was transformed into DH5α Library Efficiency Competent Cells (GibcoBRL). Transformants expressing HPPD were identified by the reddish-brown color produced when cultured overnight in LB with ampicillin.

Transformants were also prepared by transforming DH5α cells with empty pKK233-2 vector for use as a control in the enzyme assays.

B. Production of Brown Pigment and Homogentisic Acid in *E. coli*

Brown pigment formation was observed in colonies grown on solid media and in liquid cultures of *E. coli* transformed with the Arabidopsis HPPD gene. No similar brown pigmentation was associated with untransformed *E. coli* or with *E. coli* transformed with the control vector. Formation of the brown pigment (which exhibited a characteristic absorption at 450 nm) was increased by supplementing the medium with tyrosine (FIG. 2).

It is known that homogentisic acid turns brown when standing or when alkalinized and exposed to oxygen, due to the formation of an ochronotic pigment (La Du et al., in *Ocrhomosis. Pigments in Pathology*, M. Wolman (ed.), Academic Press, N.Y., 1969). Similar pigments are formed from the naturally-occurring secretion and oxidation of homogentisic acid in certain bacteria (Trias et al., *Can.J.Microbiol*. 35:1037, 1989; Goodwin et al., *Can.J.Microbiol*. 40:28, 1995). Thus, the occurrence of brown pigment suggested that *E. coli* cells transformed with the Arabidopsis HPPD gene as described above produce large amounts of homogentisic acid. Furthermore, since tyrosine is metabolized to hydroxyphenylpyruvate (thus providing additional substrate for HPPD), increased color development in the presence of increased tyrosine supports the conclusion that the brown pigment results from HPPD activity.

This was confirmed by measuring homogentisic acid directly using an HPLC-based method. The HPLC conditions for the determination of homogentisic acid were identical to those described by Denoya et al. (*J.Bacteriol*. 176:5312, 1994). The HPLC system consisted of a Waters 510 delivery module (Waters Assoc., Milford, Mass.), Waters 996 photodiode array detector, a WISP 710B automatic sampler, and a Waters 840 data integration system. A Phenomenex Spherisorb 5 ODS (1) CI8 reversed-phase column (5 mm particle size; 250×4.6 mm i.d.) was used, which was connected with a stainless steel guard column packed with C18 resin. The mobile phase (10 mM acetic acid:methanol; 85:15 v/v) was run at a flow rate of 1 ml/min. The wavelength was set at 292 nM. Culture broth samples (1 ml) were acidified by mixing with 100 ml of glacial acetic acid and were clarified by centrifugation. 50 ml of the mixture were injected on the column. The peak corresponding to homogentisic acid was compared with a homogentisic acid standard for identification and quantitation.

Figure 3B:
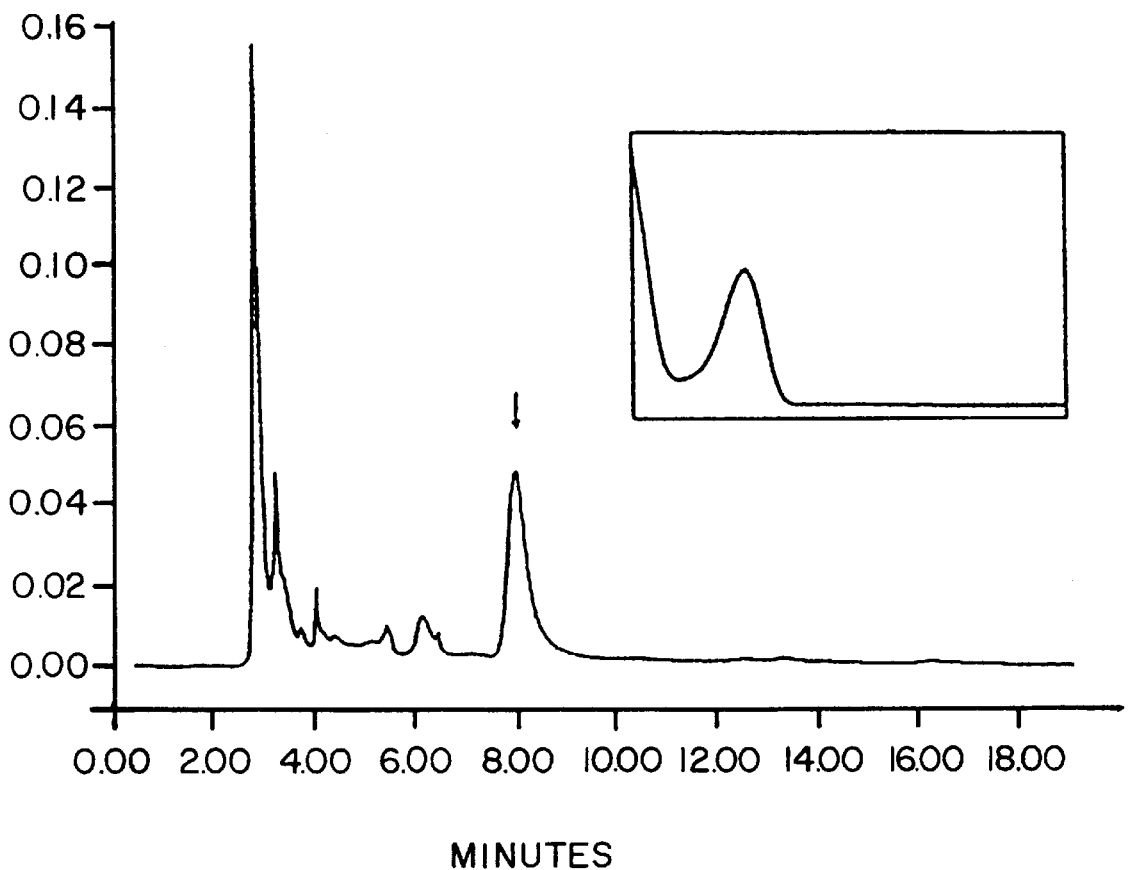

The culture medium derived from overnight cultures of control *E. coli* cells showed no trace of homogentisic acid (FIG. 3A). By contrast, HPPD-transformed *E. coli* produced a high level of homogentisic acid (FIG. 3B). The peak eluting at 8 min co-migrated with authentic homogentisic acid and had an absorption spectrum identical with authentic homogentisic acid (insert).

C. Assay of HPPD Activity

*E. coli* transformants were treated with 0.1 mg/ml lysozyme in 50 mM potassium phosphate buffer (pH 7.3) at 30° C. for 10 min. Cells were sonicated (3 times, 5 sec each, using a VibraCell sonicator, Sonics and Material, Inc., Danbury, Conn.) and the extract was subjected to centrifugation. The supernatant was desalted on an Econo-Pac 10DG column (Bio-Rad, Richmond, Calif.) that had been equilibrated with 50 mM phosphate buffer (pH 7.3). The desalted HPPD-containing extract was used for the HPPD assay.

HPPD enzymatic activity was determined by the capture of released $^{14}CO_2$ from $^{14}C$-hydroxyphenylpyruvate (Schulz et al., *FEBS Letts.* 318:162, 1993; Secor, *Plant Physiol.* 106:1429, 1994). Reactions were performed in 20 ml scintillation vials, each capped with a serum stopper through which a polypropylene well containing 50 µl of benzethonium hydroxide was suspended. Each 450 µl reaction mixture contained: 50 mM potassium phosphate buffer (pH 7.3); 50 µl of a freshly prepared 1:1 (v/v) mixture of 150 mM reduced glutathione and 3 mM dichlorophenolindophenol; 2500 units of catalase; and bacterial extract (source of HPPD). Enzyme inhibitors were added where indicated. $^{14}C$-hydroxyphenylpyruvate (50 µl of a 2 mM solution), prepared according to the method of Secor (1994, supra), was added to initiate the reaction, which proceeded at 30° C. for 30 min. The reaction was stopped by adding 100 µl 4 N sulfuric acid and the mixture was incubated for a further 30 min. The radioactivity trapped in benzethonium hydroxide was counted in a scintillation counter.

Figure 4:
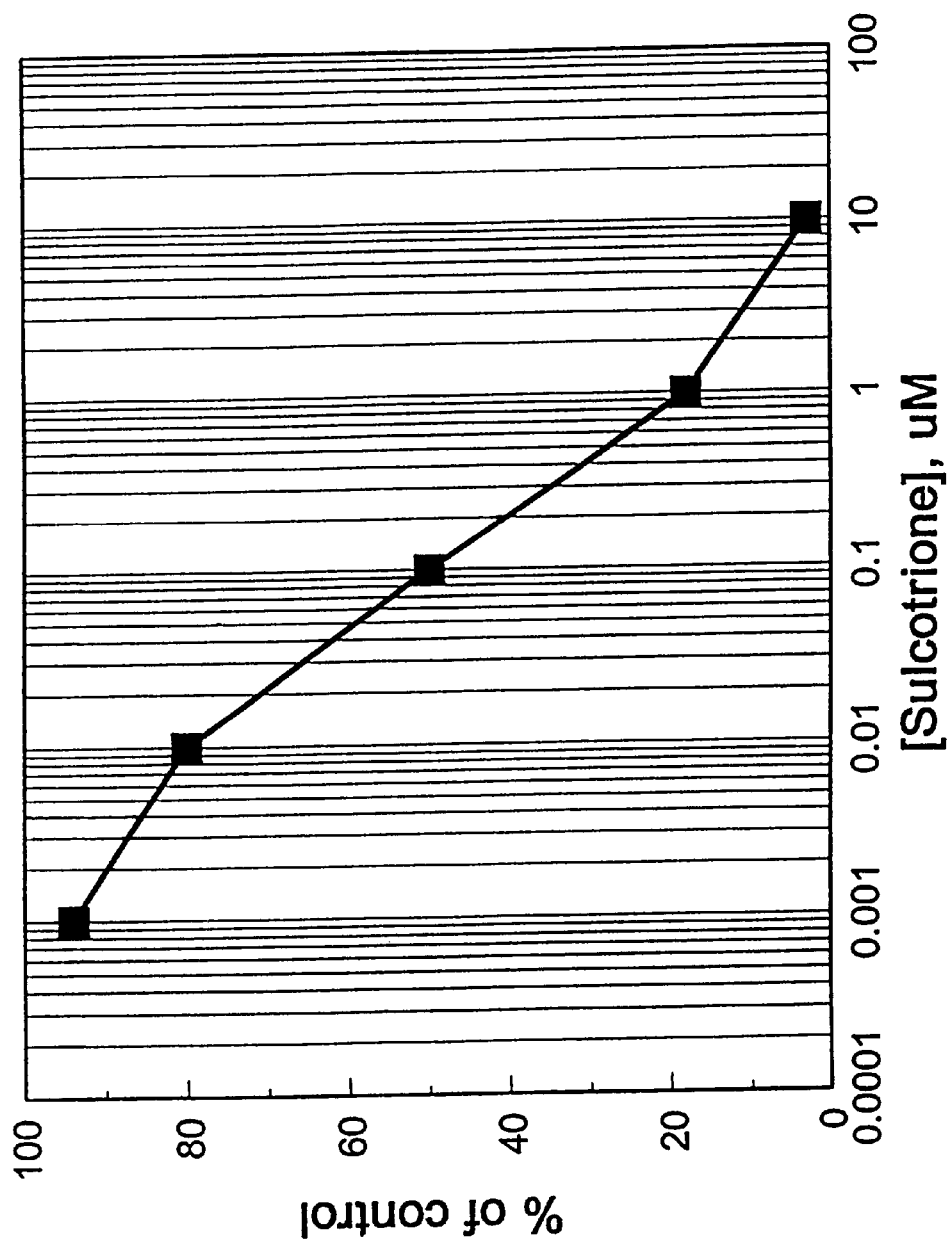
FIG. 4 is a graphic illustration of the effect of increasing concentrations of sulcotrione on the HPPD enzymatic activity of cell extracts derived from *E. coli* transformed with the Arabidopsis HPPD gene.

The results indicated that *E. coli* cells transformed with the Arabidopsis HPPD gene expressed very high levels of HPPD activity, i.e., 2.7 µmol/mg protein/hr. In contrast, HPPD activity was undetectable in untransformed or control *E. coli* cells. Furthermore, the HPPD activity was sensitive to inhibition by sulcotrione (FIG. 4). Nearly complete inhibition of the activity was observed at more than 1 µM sulcotrione. The concentration of sulcotrione required to cause 50% inhibition of the activity was 100 nM.

EXAMPLE 2

High-throughput Screening of Test Compounds to Identify HPPD Inhibitors

The following method is used in a high-throughput mode to identify HPPD inhibitors.

*E. coli* transformed with the Arabidopsis HPPD gene as described in Example 1 above is cultured overnight at 37° C. in Luria Broth with 100 µg/ml ampicillin.

1 liter of molten LB agar containing 100 µg/ml ampicillin and 1 mM tyrosine is cooled to 50° C. 0.1 ml of the overnight *E. coli* culture is then added, and 150 ml of the mixture are poured into each 9×9 sterile Sumilon biotray (Vangard International, Neptune, N.J.).

The plates are allowed to solidify and dry for 30 min. Test compounds (up to 25 µl) are applied to the test plate in sample wells (144 wells/plate, 5 cm diameter in 12×12 array) or in spots (6×96 compounds/plate). The plates are incubated overnight at 37° C.

The plates are scored by monitoring: (i) growth of *E. coli* and (ii) intensity of brown pigment. Zones in which the bacterial cells are viable but the pigment is reduced are scored as positive for HPPD inhibitors.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A purified and isolated nucleic acid which encodes the polypeptide of SEQ ID NO:1.

2. A DNA vector comprising the nucleic acid of claim 1 operably linked to a transcription regulatory element.

3. A host cell comprising the DNA vector as defined in claim 2, wherein said host cell is selected from the group consisting of a bacterial cell, a fungal cell, a plant cell, an insect cell, and a mammalian cell.

4. The cell as defined in claim 3, wherein said cell is a bacterial cell.

5. The cell as defined in claim 3, wherein said cell is a plant cell.

6. A seed comprising a plant cell comprising the DNA vector as defined in claim 2.

7. A method for identifying an HPPD inhibitor, said method comprising:

(a) incubating a cell culture transformed with and expressing the nucleic acid of claim 1 in the presence of a test compound to form a test culture, and in the absence of the test compound to form a control culture;

(b) monitoring the level of homogentisic acid, or oxidation products thereof, in said test culture and said control culture; and (c) identifying as an HPPD inhibitor any test compound that reduces the level of homogentisic acid, or oxidation products thereof, in said test culture relative to said control culture.

8. The method as defined in claim 7, wherein said cell culture is an *E. coli* cell culture.

9. The method as defined in claim 7, wherein said monitoring comprises measuring the absorbance of said test culture and said control culture at 450 nm.

10. The method as defined in claim 7, wherein said monitoring comprises detecting formation of a brown pigment.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 446 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:1:

```
Met Gly His Gln Asn Ala Ala Val Ser Glu Asn Gln Asn His Asp Asp
 1               5                  10                  15

Gly Ala Ala Ser Ser Pro Gly Phe Lys Leu Val Gly Phe Ser Lys Phe
                20                  25                  30

Val Arg Lys Asn Pro Lys Ser Asp Lys Phe Lys Val Lys Arg Phe His
            35                  40                  45

His Ile Glu Phe Trp Cys Gly Asp Ala Thr Asn Val Ala Arg Arg Phe
    50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
```

```
                        85                  90                  95
Phe Leu Phe Thr Ala Pro Tyr Ser Pro Ser Leu Ser Ala Gly Glu Ile
                100                 105                 110
Lys Pro Thr Thr Thr Ala Ser Ile Pro Ser Phe Asp His Gly Ser Cys
            115                 120                 125
Arg Ser Phe Phe Ser Ser His Gly Leu Gly Val Arg Ala Val Ala Ile
130                 135                 140
Glu Val Glu Asp Ala Glu Ser Ala Phe Ser Ile Ser Val Ala Asn Gly
145                 150                 155                 160
Ala Ile Pro Ser Ser Pro Pro Ile Val Leu Asn Glu Ala Val Thr Ile
                165                 170                 175
Ala Glu Val Lys Leu Tyr Gly Asp Val Val Leu Arg Tyr Val Ser Tyr
            180                 185                 190
Lys Ala Glu Asp Thr Glu Lys Ser Glu Phe Leu Pro Gly Phe Glu Arg
            195                 200                 205
Val Glu Asp Ala Ser Ser Phe Pro Leu Asp Tyr Gly Ile Arg Arg Leu
        210                 215                 220
Asp His Ala Val Gly Asn Val Pro Glu Leu Gly Pro Ala Leu Thr Tyr
225                 230                 235                 240
Val Ala Gly Phe Thr Gly Phe His Gln Phe Ala Glu Phe Thr Ala Asp
                245                 250                 255
Asp Val Gly Thr Ala Glu Ser Gly Leu Asn Ser Ala Val Leu Ala Ser
                260                 265                 270
Asn Asp Glu Met Val Leu Leu Pro Ile Asn Glu Pro Val His Gly Thr
            275                 280                 285
Lys Arg Lys Ser Gln Ile Gln Thr Tyr Leu Glu His Asn Glu Gly Ala
290                 295                 300
Gly Leu Gln His Leu Ala Leu Met Ser Glu Asp Ile Phe Arg Thr Leu
305                 310                 315                 320
Arg Glu Met Arg Lys Arg Ser Ser Ile Gly Gly Phe Asp Phe Met Pro
                325                 330                 335
Ser Pro Pro Pro Thr Tyr Tyr Gln Asn Leu Lys Lys Arg Val Gly Asp
                340                 345                 350
Val Leu Ser Asp Asp Gln Ile Lys Glu Cys Glu Glu Leu Gly Ile Leu
            355                 360                 365
Val Asp Arg Asp Asp Gln Gly Thr Leu Leu Gln Ile Phe Thr Lys Pro
370                 375                 380
Leu Gly Asp Asp Arg Pro Thr Ile Phe Ile Glu Ile Ile Gln Arg Val
385                 390                 395                 400
Gly Cys Met Met Lys Asp Glu Glu Gly Lys Ala Tyr Gln Ser Gly Gly
                405                 410                 415
Cys Gly Gly Phe Gly Lys Gly Asn Phe Ser Glu Leu Phe Lys Ser Ile
                420                 425                 430
Glu Glu Tyr Glu Lys Thr Leu Glu Ala Lys Gln Leu Val Gly
            435                 440                 445

(2) INFORMATION FOR SEQ ID NO:2:

(i) SEQUENCE CHARACTERISTICS:
        (A) LENGTH: 392 amino acids
        (B) TYPE: amino acid
        (C) STRANDEDNESS: single
        (D) TOPOLOGY: linear (ii) MOLECULE TYPE: None
```

(xi) SEQUENCE DESCRIPTION: SEQ ID NO:2:

```
Met Thr Thr Tyr Asn Asn Lys Gly Pro Lys Pro Glu Arg Gly Arg Phe
 1               5                  10                  15

Leu His Phe His Ser Val Thr Phe Trp Val Gly Asn Ala Lys Gln Ala
                20                  25                  30

Ala Ser Phe Tyr Cys Asn Lys Met Gly Phe Glu Pro Leu Ala Tyr Arg
            35                  40                  45

Gly Leu Glu Thr Gly Ser Arg Glu Val Val Ser His Val Ile Lys Arg
        50                  55                  60

Gly Lys Ile Val Phe Val Leu Cys Ser Ala Leu Asn Pro Trp Asn Lys
 65                  70                  75                  80

Glu Met Gly Asp His Leu Val Lys Gly Asp Gly Val Lys Asp Ile Ala
                85                  90                  95

Phe Glu Val Glu Asp Cys Asp His Ile Val Gln Lys Ala Arg Glu Arg
                100                 105                 110

Gly Ala Lys Ile Val Arg Glu Pro Trp Val Glu Gln Asp Lys Phe Gly
            115                 120                 125

Lys Val Lys Phe Ala Val Leu Gln Thr Tyr Gly Asp Thr Thr His Thr
        130                 135                 140

Leu Val Glu Lys Ile Asn Tyr Thr Gly Arg Phe Leu Pro Gly Phe Glu
145                 150                 155                 160

Ala Pro Thr Tyr Lys Asp Thr Leu Leu Pro Lys Leu Pro Arg Cys Asn
                165                 170                 175

Leu Glu Ile Ile Asp His Ile Val Gly Asn Gln Pro Asp Gln Glu Met
                180                 185                 190

Gln Ser Ala Ser Glu Trp Tyr Leu Lys Asn Leu Gln Phe His Arg Phe
            195                 200                 205

Trp Ser Val Asp Asp Thr Gln Val His Thr Glu Tyr Ser Ser Leu Arg
        210                 215                 220

Ser Ile Val Val Thr Asn Tyr Glu Glu Ser Ile Lys Met Pro Ile Asn
225                 230                 235                 240

Glu Pro Ala Pro Gly Arg Lys Lys Ser Gln Ile Gln Glu Tyr Val Asp
                245                 250                 255

Tyr Asn Gly Gly Ala Gly Val Gln His Ile Ala Leu Lys Thr Glu Asp
                260                 265                 270

Ile Ile Thr Ala Ile Arg His Leu Arg Glu Arg Gly Thr Glu Phe Leu
            275                 280                 285

Ala Ala Pro Ser Ser Tyr Tyr Lys Leu Leu Arg Glu Asn Leu Lys Ser
        290                 295                 300

Ala Lys Ile Gln Val Lys Glu Ser Met Asp Val Leu Glu Glu Leu His
305                 310                 315                 320

Ile Leu Val Asp Tyr Asp Glu Lys Gly Tyr Leu Leu Gln Ile Phe Thr
                325                 330                 335

Lys Pro Met Gln Asp Arg Pro Thr Leu Phe Leu Glu Val Ile Gln Arg
                340                 345                 350

His Asn His Gln Gly Phe Gly Ala Gly Asn Phe Asn Ser Leu Phe Lys
            355                 360                 365

Ala Phe Glu Glu Glu Gln Ala Leu Arg Gly Asn Leu Thr Asp Leu Glu
        370                 375                 380

Pro Asn Gly Val Arg Ser Gly Met
385                 390
```

(2) INFORMATION FOR SEQ ID NO:3:

(i) SEQUENCE CHARACTERISTICS:
    (A) LENGTH: 393 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO:3:

```
Met Thr Thr Tyr Ser Asp Lys Gly Ala Lys Pro Glu Arg Gly Arg Phe
 1               5                  10                  15

Leu His Phe His Ser Val Thr Phe Trp Val Gly Asn Ala Lys Gln Ala
                 20                  25                  30

Ala Ser Phe Tyr Cys Ser Lys Met Gly Phe Glu Pro Leu Ala Tyr Arg
             35                  40                  45

Gly Leu Glu Thr Gly Ser Arg Glu Val Val Ser His Val Ile Lys Gln
         50                  55                  60

Gly Lys Ile Val Phe Val Leu Ser Ser Ala Leu Asn Pro Trp Asn Lys
 65                  70                  75                  80

Glu Met Gly Asp His Leu Val Lys His Gly Asp Gly Val Lys Asp Ile
                 85                  90                  95

Ala Phe Glu Val Glu Asp Cys Asp Tyr Ile Val Gln Lys Ala Arg Glu
            100                 105                 110

Arg Gly Ala Lys Ile Met Arg Glu Pro Trp Val Glu Gln Asp Lys Phe
        115                 120                 125

Gly Lys Val Lys Phe Ala Val Leu Gln Thr Tyr Gly Asp Thr Thr His
130                 135                 140

Thr Leu Val Glu Lys Met Asn Tyr Ile Gly Gln Phe Leu Pro Gly Tyr
145                 150                 155                 160

Glu Ala Pro Ala Phe Met Asp Pro Leu Leu Pro Lys Leu Pro Lys Cys
                165                 170                 175

Ser Leu Glu Met Ile Asp His Ile Val Gly Asn Gln Pro Asp Gln Glu
            180                 185                 190

Met Val Ser Ala Ser Glu Trp Tyr Leu Lys Asn Leu Gln Phe His Arg
        195                 200                 205

Phe Trp Ser Val Asp Asp Thr Gln Val His Thr Glu Tyr Ser Ser Leu
210                 215                 220

Arg Ser Ile Val Val Ala Asn Tyr Glu Glu Ser Ile Lys Met Pro Ile
225                 230                 235                 240

Asn Glu Pro Ala Pro Gly Lys Lys Ser Gln Ile Gln Glu Tyr Val
                245                 250                 255

Asp Tyr Asn Gly Gly Ala Gly Val Gln His Ile Ala Leu Lys Thr Glu
            260                 265                 270

Asp Ile Ile Thr Ala Ile Arg His Leu Arg Glu Arg Gly Leu Glu Phe
        275                 280                 285

Leu Ser Val Pro Ser Thr Tyr Tyr Lys Gln Leu Arg Glu Lys Leu Lys
290                 295                 300

Thr Ala Lys Ile Lys Val Lys Glu Asn Ile Asp Ala Leu Glu Glu Leu
305                 310                 315                 320

Lys Ile Leu Val Asp Tyr Asp Gly Lys Gly Tyr Leu Leu Gln Ile Phe
                325                 330                 335

Thr Lys Pro Val Gln Asp Arg Pro Thr Leu Phe Leu Glu Val Ile Gln
            340                 345                 350

Arg His Asn His Gln Gly Phe Gly Ala Gly Asn Phe Asn Ser Leu Phe
        355                 360                 365
```

-continued

```
Lys Ala Phe Glu Glu Gln Asn Leu Arg Gly Asn Leu Thr Asn Met
    370                 375                 380

Glu Thr Asn Gly Val Val Pro Gly Met
385                 390

(2) INFORMATION FOR SEQ ID NO:4:

(i) SEQUENCE CHARACTERISTICS:
        (A) LENGTH: 393 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

Met Thr Ser Tyr Ser Asp Lys Gly Glu Lys Pro Glu Arg Gly Arg Phe
1               5                   10                  15

Leu His Phe His Ser Val Thr Phe Trp Val Gly Asn Ala Lys Gln Ala
                20                  25                  30

Ala Ser Tyr Tyr Cys Ser Lys Ile Gly Phe Glu Pro Leu Ala Tyr Lys
            35                  40                  45

Gly Leu Glu Thr Gly Ser Arg Glu Val Val Ser His Val Val Lys Gln
50                  55                  60

Asp Lys Ile Val Phe Val Phe Ser Ser Ala Leu Asn Pro Trp Asn Lys
65                  70                  75                  80

Glu Met Gly Asp His Leu Val Lys His Gly Asp Gly Val Lys Asp Ile
                85                  90                  95

Ala Phe Glu Val Glu Asp Cys Asp Tyr Ile Val Gln Lys Ala Arg Glu
            100                 105                 110

Arg Gly Ala Ile Ile Val Arg Glu Glu Val Cys Cys Ala Ala Asp Val
            115                 120                 125

Arg Gly His His Thr Pro Leu Asp Arg Ala Arg Gln Val Trp Glu Gly
130                 135                 140

Thr Leu Val Glu Lys Met Thr Phe Cys Leu Asp Ser Arg Pro Gln Pro
145                 150                 155                 160

Ser Gln Thr Leu Leu His Arg Leu Leu Leu Ser Lys Leu Pro Lys Cys
                165                 170                 175

Gly Leu Glu Ile Ile Asp His Ile Val Gly Asn Gln Pro Asp Gln Glu
            180                 185                 190

Met Glu Ser Ala Ser Gln Trp Tyr Met Arg Asn Leu Gln Phe His Arg
            195                 200                 205

Phe Trp Ser Val Asp Asp Thr Gln Ile His Thr Glu Tyr Ser Ala Leu
            210                 215                 220

Arg Ser Val Val Met Ala Asn Tyr Glu Glu Ser Ile Lys Met Pro Ile
225                 230                 235                 240

Asn Glu Pro Ala Pro Gly Lys Lys Ser Gln Ile Gln Glu Tyr Val
                245                 250                 255

Asp Tyr Asn Gly Gly Ala Gly Val Gln His Ile Ala Leu Lys Thr Glu
            260                 265                 270

Asp Ile Ile Thr Ala Ile Arg Ser Leu Arg Glu Arg Gly Val Glu Phe
            275                 280                 285

Leu Ala Val Pro Phe Thr Tyr Tyr Lys Gln Leu Gln Glu Lys Leu Lys
            290                 295                 300

Ser Ala Lys Ile Arg Val Lys Glu Ser Ile Asp Val Leu Glu Glu Leu
305                 310                 315                 320
```

```
Lys Ile Leu Val Asp Tyr Asp Glu Lys Gly Tyr Leu Leu Gln Ile Phe
                325                 330                 335

Thr Lys Pro Met Gln Asp Arg Pro Thr Val Phe Leu Glu Val Ile Gln
                340                 345                 350

Arg Asn Asn His Gln Gly Phe Gly Ala Gly Asn Phe Asn Ser Leu Phe
                355                 360                 365

Lys Ala Phe Glu Glu Gln Glu Leu Arg Gly Asn Leu Thr Asp Thr
370             375                 380

Asp Pro Asn Gly Val Pro Phe Arg Leu
385             390
```

(2) INFORMATION FOR SEQ ID NO:5:

(i) SEQUENCE CHARACTERISTICS:
        (A) LENGTH: 378 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

```
Met Thr Gln Thr Thr His His Thr Pro Asp Thr Ala Arg Gln Ala Asp
1               5                   10                  15

Pro Phe Pro Val Lys Gly Met Asp Ala Val Phe Ala Val Gly Asn
                20                  25                  30

Ala Lys Gln Ala Ala His Tyr Ser Thr Ala Phe Gly Met Gln Leu Val
                35                  40                  45

Ala Tyr Ser Gly Pro Glu Asn Gly Ser Arg Glu Thr Ala Ser Tyr Val
50                  55                  60

Leu Thr Asn Gly Ser Ala Arg Phe Val Leu Thr Ser Val Ile Lys Pro
65                  70                  75                  80

Ala Thr Pro Trp Gly His Phe Leu Ala Asp His Val Ala Glu His Gly
                85                  90                  95

Asp Gly Val Val Asp Leu Ala Ile Glu Val Pro Asp Ala Arg Ala Ala
                100                 105                 110

His Ala Tyr Ala Ile Glu His Gly Ala Arg Ser Val Ala Glu Pro Tyr
                115                 120                 125

Glu Leu Lys Asp Glu His Gly Thr Val Val Leu Ala Ala Ile Ala Thr
130                 135                 140

Tyr Gly Lys Thr Arg His Thr Leu Val Asp Arg Gly Tyr Asp Gly Pro
145                 150                 155                 160

Tyr Leu Pro Gly Tyr Val Ala Ala Pro Ile Val Glu Pro Pro Ala
                165                 170                 175

His Arg Thr Phe Gln Ala Ile Asp His Cys Val Gly Asn Val Glu Leu
                180                 185                 190

Gly Arg Met Asn Glu Trp Val Gly Phe Tyr Asn Lys Met Gly Phe Thr
                195                 200                 205

Asn Met Lys Glu Phe Val Gly Asp Ile Ala Thr Glu Tyr Ser Ala
210                 215                 220

Leu Met Ser Lys Val Val Ala Asp Gly Thr Leu Lys Val Lys Phe Pro
225                 230                 235                 240

Ile Asn Glu Pro Ala Leu Ala Lys Lys Ser Gln Ile Asp Glu Tyr
                245                 250                 255

Leu Glu Phe Tyr Gly Gly Ala Gly Val Gln His Ile Ala Leu Asn Thr
                260                 265                 270
```

```
Gly Asp Ile Val Glu Thr Val Arg Thr Met Arg Ala Ala Gly Val Gln
        275                 280                 285

Phe Leu Asp Thr Pro Asp Ser Tyr Tyr Asp Thr Leu Gly Glu Trp Val
        290                 295                 300

Gly Asp Thr Arg Val Pro Val Asp Thr Leu Arg Glu Leu Lys Ile Leu
305                 310                 315                 320

Ala Asp Arg Asp Glu Asp Gly Tyr Leu Leu Gln Ile Phe Thr Lys Pro
                325                 330                 335

Val Gln Asp Arg Pro Thr Val Phe Phe Glu Ile Ile Glu Arg His Gly
            340                 345                 350

Ser Met Gly Phe Gly Lys Gly Asn Phe Lys Ala Leu Phe Glu Ala Ile
        355                 360                 365

Glu Arg Glu Gln Glu Lys Arg Gly Asn Leu
    370                 375
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:6:

CGTGCTCAGC GATGATCAGA                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

CGGCCTGTCA CCTAGTGGTT                                              20

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

CTTCTACCGA TTAACGAGCC AGTG                                         24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:9:

CACTGGCTCG TTAATCGGTA GAAG                                         24

(2) INFORMATION FOR SEQ ID NO:10:

(i) SEQUENCE CHARACTERISTICS:
        (A) LENGTH: 24 base pairs (B) TYPE: nucleic acid
        (C) STRANDEDNESS: single
        (D) TOPOLOGY: linear (xi) SEQUENCE DESCRIPTION: SEQ ID NO:10:

TCCATCACAT CGAGTTCTGG TGCG                                  24

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:11:

AAAAGGAATC GGAGGTCACC GGA                                   23

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

CTGAGGTTAA ACTATACGGC GA                                    22

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:13:

TCGCCGTATA GTTTAACCTC AG                                    22

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:14:

CCATGGGCCA CCAAAACG                                         18

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:15:

VYHVSHYVSY VVVSVYSSVY HYYYH 25

(2) INFORMATION FOR SEQ ID NO:16:

(i) SEQUENCE CHARACTERISTICS:
(A) LENGTH: 21 base pairs
(B) TYPE: nucleic acid

```
        (C) STRANDEDNESS: single
        (D) TOPOLOGY: linear (xi) SEQUENCE DESCRIPTION: SEQ ID NO:16:

GAAATCCATG GCACCAAAAC G                                          21

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CTTCTCCATG GTCATCCCAC TAACTGT                                    27

(2) INFORMATION FOR SEQ ID NO:18:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CAAGAAACGN GTGGNCGACG TGCTCAGCGA TGATCAGATC AAGGAGTGTG AGGAATTAGG    60

GATTCTTNTA GACAGAGATG ATCAAGGGAC GTTNCTTCAA ATCTNCACAA AACCACTAGG   120

TGACAGGCCG ACGNTATTTA TAGAGATAAT CCAGAGNGTA GGATGCATGA TGAAAGATGT   180

GGAAGGGANG GCTTACCAGA GTGGAGNATN GGCAAAGGCA ATT                    223
```